United States Patent [19]

Hosokawa

[11] Patent Number: 5,641,894
[45] Date of Patent: Jun. 24, 1997

[54] PROCESS AND APPARATUS FOR FILTRATE MEASUREMENT

[75] Inventor: Kazutaka Hosokawa, Kanagawa, Japan

[73] Assignee: Koei Industry Co., Ltd., Kanagawa, Japan

[21] Appl. No.: 590,111

[22] Filed: Jan. 23, 1996

[30] Foreign Application Priority Data

Jan. 26, 1995 [JP] Japan ................... 7-029931

[51] Int. Cl.$^6$ ............................................ G01N 1/10
[52] U.S. Cl. ................ 73/64.56; 73/863.23; 73/863.24; 73/863.84; 73/864.81
[58] Field of Search ..................... 73/53.01, 53.03, 73/61.41, 61.43, 61.59, 64.56, 863.23, 863.24, 863.81, 863.83, 863.84, 864.81

[56] References Cited

U.S. PATENT DOCUMENTS

| 4,262,533 | 4/1981 | Jaeger ................... 73/863.83 X |
| 4,269,064 | 5/1981 | Johnson et al. ................... 73/863.82 |
| 4,630,479 | 12/1986 | Wagener et al. ................... 73/863.83 |

FOREIGN PATENT DOCUMENTS

| 1215962 | 5/1966 | Germany . |
| 678844 | 11/1994 | Japan . |

OTHER PUBLICATIONS

Copy of Article in Japanese for the product "Samplex" of Kawani Co. Ltd. with English summary, no date.

*Primary Examiner*—Michael Brock
*Attorney, Agent, or Firm*—Michael D. Bednarek; Kilpatrick Stockton LLP

[57] ABSTRACT

A sampling cylinder 3 is attached to a process piping 2 through which a slurry flows. A front piston 9 and a rear piston 10 which slide within the sampling cylinder 3 are driven via a driving rod 12 by a fluid pressure cylinder 11. These two pistons 9,10 are allowed to slide to collect the slurry into a sampling space 30 defined between the pistons 9,10. The front piston 9 is brought closer to the rear piston 10 to reduce the volume of the sampling space 30. Thus, only the filtrate in the slurry is fed through a filter 5 into a filtrate collecting tank 6, where pH etc. of the filtrate is measured by a sensor 8. Subsequently, the front piston 9 is brought apart from the rear piston 10 to increase the volume of the sampling space 30. Thus, the filtrate is returned into the sampling space 30 back-washing the filter 5. Then, the slurry in the sampling space 30 is returned to the process piping 2.

24 Claims, 8 Drawing Sheets

PROCESS AND APPARATUS FOR FILTRATE MEASUREMENT

BACKGROUND OF THE INVENTION

1. Field of the Invention

The present invention relates to a process and an apparatus for collecting only the filtrate from a slurry of raw pulp and the like, and for measuring pH, conductivity, etc. of the filtrate.

2. Description of the Prior Art

For example, there is known as a filtrate measuring apparatus for collecting a pulp filtrate to measure its pH etc., one as disclosed in a Japanese Utility Model Application under Laid-open No. Hei 6-78844, containing a filtrate sampling pipe connected to a raw-pulp feeding process piping and having a filter attached to the tip of the pipe; a piston disposed to be slidable within the filtrate sampling pipe, which collects a filtrate into the filtrate sampling pipe in a retracting stroke away from the filter and also back-washing the filter in an approaching stroke toward the filter; a detection tank connected via a closing valve to the filter sampling pipe and to which tank the sample filtrate is fed; a detector disposed in this detection tank; and a flush valve which is connected to the filtrate sampling pipe and feeds a wash water through the filtrate collecting pipe and the closing valve to the detection tank.

In the prior art filtrate measuring apparatus described above, only the filtrate is adapted to be collected into the apparatus as the piston slides, so that the apparatus advantageously has a simple structure and can clean fully the inside of the apparatus in a short time. However, since the filter is constantly brought into contact with the slurry fed through the process piping, some kinds of slurry will deposit the the solid content contained in the slurry on the outer side of the filter even if the filter is closed on the inner side by the piston and will cause clogging of the filter. Further, the property of slurry is liable to be changed corresponding to the amount of sample slurry.

SUMMARY OF THE INVENTION

The present invention is accomplished in view of such present circumstances, and it is an objective of the present invention to provide a filtrate measuring process which is free from filter clogging and from change in the properties of the slurry attributed to the filtrate measurement, irrespective of the kind of slurry, as well as, to provide an apparatus for practicing the process.

It is another objective of the present invention to facilitate post-treatment of the sample slurry.

It is another objective of the present invention to improve accuracy of the filtrate measurement.

It is another objective of the present invention to simplify the structure of the sampling mechanism.

It is another objective of the present invention to achieve driving of a front piston and a rear piston with a single driving source.

It is still another objective of the present invention to prevent clogging of a cleaning nozzle.

It is a further objective of the present invention to facilitate treatment of the resulting wash water.

In order to attain the intended objectives described above, the present invention provides a filtrate measuring process which comprises employing a sampling cylinder connected to a process piping for feeding a slurry, a filtrate collecting tank connected via a filter to the sampling cylinder, a filtrate measuring sensor attached to the inside of the filtrate collecting tank and a sampling mechanism which has a sampling space and which slides within the sampling cylinder; collecting a predetermined amount of slurry from the process piping to the sampling space; reducing the volume of the sampling space to feed only the filtrate in the sample slurry to the filtrate collecting tank where measurement of the filtrate is performed; and expanding the volume of the sampling space to return the filtrate in the filtrate collecting tank to the sampling space under back-washing of the filter with the filtrate.

The present invention also provides a filtrate measuring process, wherein the sample slurry in the sampling space which is recombined with the filtrate in the filtrate collecting tank is returned to the process piping.

The present invention also provides a filtrate measuring process, wherein the sensor is cleaned with wash water after the filtrate measurement, and the resulting wash water is discharged outside the process piping.

The present invention also provides a filtrate measuring apparatus comprising a sampling cylinder connected to a process piping for feeding a slurry; a filtrate collecting tank connected via a filter to the sampling cylinder; a filtrate measuring sensor attached to the inside of the filtrate collecting tank; and a sampling mechanism which contains a sampling space and which slides within the sampling cylinder to collect a slurry from the process piping into the sampling space and to return the collected sample slurry to the process piping, as well as, to feed the filtrate in the sample slurry to the filtrate collecting tank and to return the filtrate in the filtrate collecting tank into the sampling space by expanding or reducing the volume of the sampling space.

The present invention also provides a filtrate measuring apparatus, wherein the sampling mechanism has a front piston which reciprocates between the sampling cylinder and the process piping, and a rear piston which reciprocates within the sampling cylinder; the two pistons and the sampling cylinder defining the sampling space.

The present invention also provides a filtrate measuring apparatus, wherein the sampling mechanism contains a driving rod which slidably penetrates the rear piston and is connected at the front end to the front piston to reciprocate the front piston; a rod stopper provided on the driving rod, which is abutted against the rear side of the rear piston when the driving rod is advanced toward the process piping; a first magnet which is provided at least on one of the rod stopper and the rear piston, for magnetically attracting the rear piston to the rod stopper; a cylinder stopper provided on the sampling cylinder, to which the rear side of the rear piston is abutted when the driving rod is retracted; and a second magnet, which is provided at least on one of the cylinder stopper and the rear piston, for magnetically attracting the rear piston to the cylinder stopper.

The present invention also provides a filtrate measuring apparatus, wherein the sampling mechanism contains a driving rod which slidably penetrates the rear piston and is connected at the front end to the front piston to reciprocate the front piston; a rod stopper provided on the driving rod, which is abutted against the rear side of the rear piston when the driving rod is advanced toward the process piping; a spring holder extended backwardly from the rear side of the rear piston by a predetermined length; and a spring retained between the spring holder and the rod stopper.

The present invention also provides a filtrate measuring apparatus, wherein the filtrate collecting tank has a cleaning means for cleaning the sensor after filtrate measurement.

The present invention also provides a filtrate measuring apparatus, wherein the cleaning means contains a cleaning nozzle for injecting wash water; a plug for opening and closing the tip of the cleaning nozzle; and a spring for normally urging the plug in the closing direction; the plug being let open against the urging force of the spring by the discharge pressure of the wash water.

The present invention also provides a filtrate measuring apparatus, wherein the sampling cylinder is disposed horizontally, and the filtrate collecting tank is connected via a filter onto the upper side of the sampling cylinder; with a discharge section being provided on the lower side of the sampling cylinder, through which the washing resulted after cleaning of the sensor is discharged via the filter and the sampling cylinder.

In the present invention, a predetermined amount of slurry is collected from the process piping to the sampling space under the sliding motion of the sampling mechanism, and the volume of the sampling space is reduced to feed the filtrate only in the sample slurry to the filtrate collecting tank where the filtrate is measured. Then the sampling space is expanded to return the filtrate in the filtrate collecting tank to the sampling space, while the filter is back-washed with the returning filtrate. Accordingly, unlike the case where the filtrate only is sampled into the apparatus, properties of the slurry contained in the process piping remain unchanged, and besides the filter can be constantly maintained clean by the back-washing. In addition, since the filter is kept away from contact with the slurry flowing through the process piping, the solid content in the slurry does not inconveniently deposit on the filter to cause clogging, irrespective of the kind of slurry.

In the present invention, the sample slurry staying in the sampling space recombined with the filtrate in the filtrate collecting tank is returned to the process piping. Accordingly, post-treatment is easier compared with the cases where the sample slurry is discharged to other places to be treated there, and also the amount of slurry to be forwarded through the process piping to the subsequent step does not inconveniently decrease.

In the present invention, the sensor having completed a filtrate measurement is cleaned with wash water, and the resulting wash water is discharged to the outside of the process piping. Accordingly, not only accuracy of filtrate measurement can be improved but also properties of the slurry in the process piping are not changed by the cleaning treatment.

In the present invention, the sampling mechanism which slides within the sampling cylinder performs not only collection of the slurry from the process piping to the sampling space and returning of the sample slurry to the process piping but also feeding of the filtrate in the sample slurry to the filtrate collecting tank and returning of the filtrate in the filtrate collecting tank to the sampling space. Accordingly, all sorts of slurry filtrates can be measured accurately using the simple structure, and the filter can be constantly maintained clean. In addition, post-treatment of the sample slurry is easy.

In the present invention, the sampling mechanism contains a front piston and a rear piston, and these pistons constitute together with the sampling cylinder the sampling space. Accordingly, the slurry can be collected into the sampling space and returned to the process piping merely by reciprocating these two pistons, and also the volume of the sampling space can be increased or reduced by merely changing the span between these pistons, thus the structure is simplified.

In the present invention, the front piston is directly driven by a driving rod; whereas the rear piston is driven indirectly by the driving rod via a first magnet and a second magnet, or driven indirectly via the spring provided between the spring holder and the rod stopper. Accordingly, these two pistons, which are of different actions, can be driven by the driving rod only.

In the present invention, the filtrate collecting tank is provided with a cleaning means for cleaning the sensor after completion of each filtrate measurement. Accordingly, even if the sensor is contaminated by the previous run of filtrate measurement, the measurement accuracy can be improved without adversely affecting the next run.

In the present invention, the tip of the cleaning nozzle is closed with a plug. Accordingly, the nozzle is not inconveniently clogged to be prevented from duly performing cleaning, even if the nozzle is situated at such a position as it is submerged in the filtrate.

In the present invention, the sampling cylinder is disposed horizontally, and the filtrate collecting tank is connected via the filter onto the upper side of the cylinder, with the discharge section being provided on the bottom side of the sampling cylinder. Accordingly, the wash water supplied from the cleaning means and having cleaned the sensor flows through the filter into the sampling cylinder to be discharged from the discharge section, so that not only treatment of the resulting wash water is facilitated but also the filter can be cleaned.

DETAILED DESCRIPTION OF THE PREFERRED EMBODIMENTS

The present invention will be described referring to the attached drawings.

Figure 1:
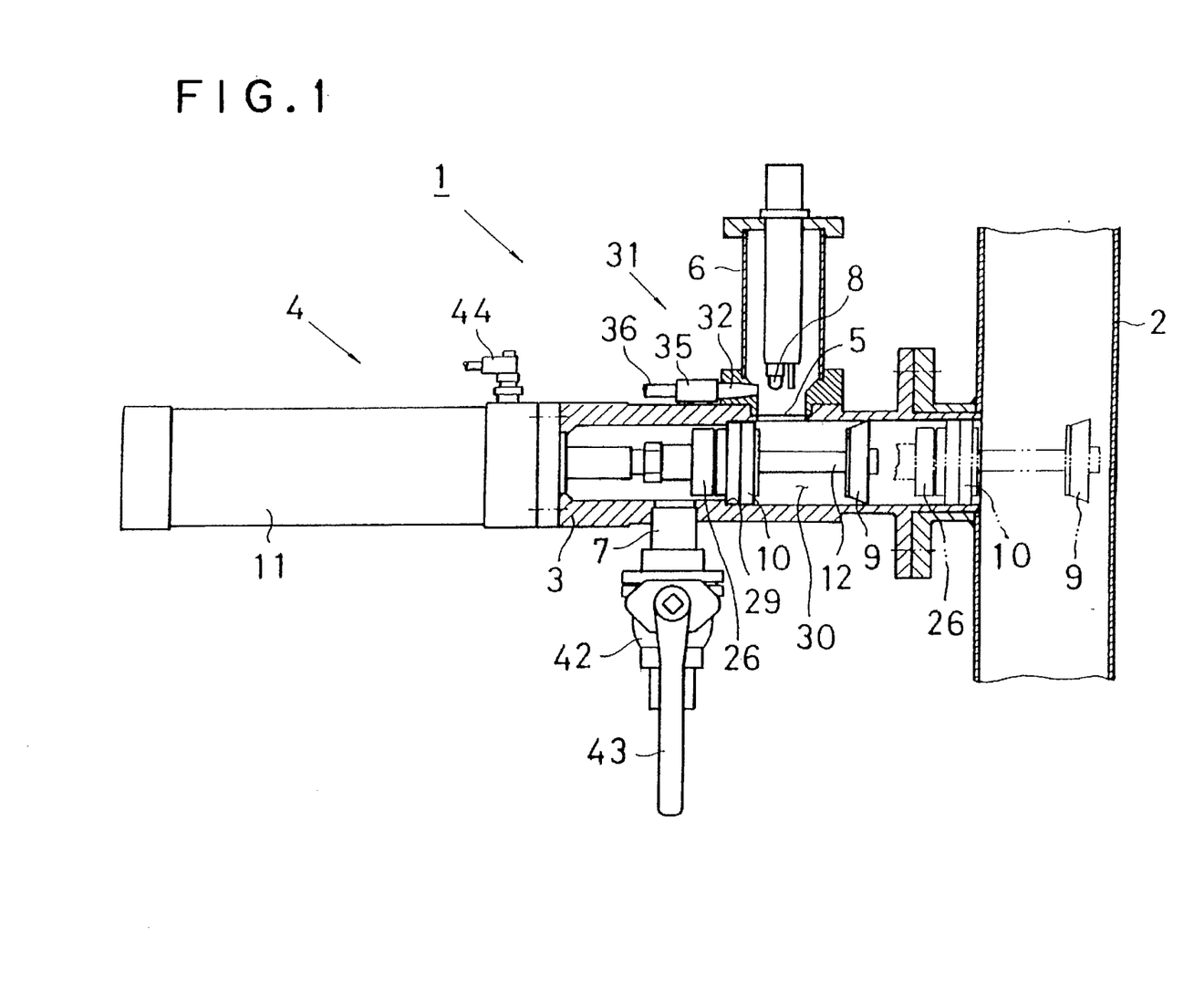
FIG. 1 is a partial cross-sectional view showing an embodiment of the filtrate measuring apparatus according to the present invention.

FIG. 1 shows an embodiment of the filtrate measuring apparatus according to the present invention. The filtrate measuring apparatus 1 contains a sampling cylinder 3 connected orthogonally to a vertical process piping 2 for feeding a slurry of raw pulp and the like. To the sampling cylinder 3 are attached a sampling mechanism 4, a filter 5, a filtrate collecting tank 6 and a washing discharge pipe 7. The slurry flowing through the process piping 2 is collected in a predetermined amount into the sampling cylinder 3 by the sampling mechanism 4, and only the filtrate in the sample slurry is fed to the filtrate collecting tank 6, where pH, conductivity, etc. of the filtrate are designed to be measured by a sensor 8 detachably disposed in the tank 6.

Figure 2:
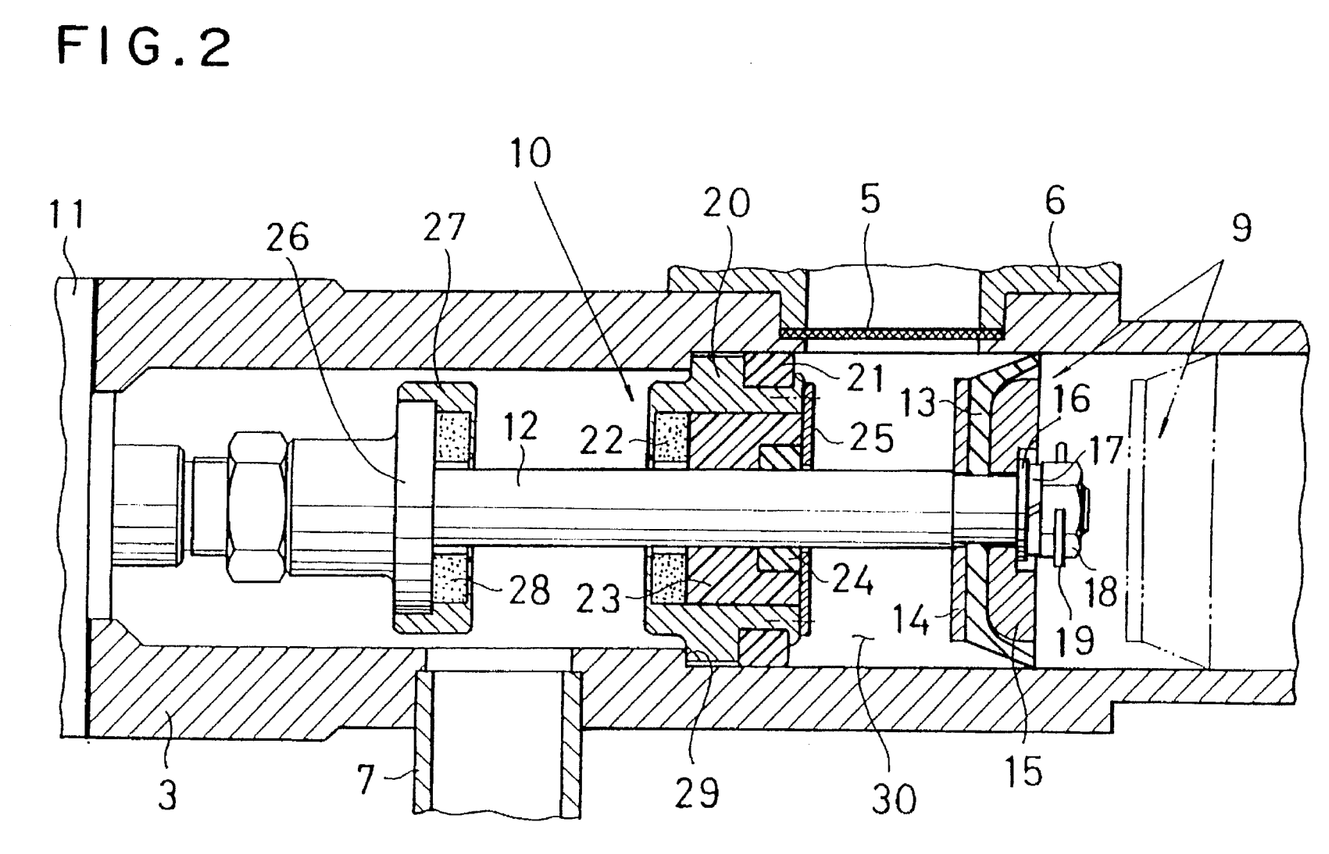
FIG. 2 is a detail view of a major portion in FIG. 1.

The sampling mechanism 4 is provided with a front piston 9 which reciprocates in and between the sampling cylinder 3 and the process piping 2, a rear piston 10 which reciprocates in the sampling cylinder 3, a fluid pressure cylinder 11 fixed to the rear end of the sampling cylinder 3 and a driving rod 12 which transmits driving force of the fluid pressure cylinder 11 to the respective pistons 9,10, as shown in FIGS. 1 and 2. These pistons 9,10 are adapted to be operated in different manners merely by advancing and retracting the driving rod 12 as will be detailed later.

Specifically, the front piston 9 consists of a packing 13, e.g., made of rubber, attached to the front end of the driving rod 12, supporting members 14,15 sandwiching the packing 13 therebetween, a nut 18 clamping these members 13,14,15 together via a washer 16 and a spring washer 17, and a locking pin 19 for locking the nut 18, as shown in FIG. 2. The driving force of the driving rod 12 is transmitted directly to the front piston 9. Thus, the front piston 9 reciprocates between a back dead center as indicated by a solid line in FIG. 2 and the front dead center as indicated by a two dot-and-dashed line in FIG. 1.

The rear piston 10 consists of a piston main body 20 made of a magnetic material, a packing 21, e.g., made of rubber, fitted around the circumference of the piston main body 20, an annular magnet 22 disposed in the piston main body 20, a bearing 23, e.g., made of synthetic resin, a seal ring 24, e.g., made of rubber, and a doughnut-type supporting plate 25 for retaining these members within the piston main body 20, as shown in FIG. 2. The driving rod 12 slidably penetrates the center of the rear piston 10.

A rod stopper 26 is fixed to the driving rod 12 behind the rear piston 10, and an annular magnet 28 is attached to the front side of the rod stopper 26 via a fitting cover 27 made of a magnetic material. This rod stopper 26 is abutted against the rear side of the rear piston 10 in the stroke that the front piston 9 is moved from the back dead center to the front dead center, and magnetically attract the rear piston 10 with the aid of the magnets 22,28 in the abutted state, so that the rear piston 10 can be moved together with the front piston 9 to the front dead center.

When the front piston 9 locating at the front dead center is to be moved to the back dead center, the front piston 9 and the rear piston 10 move together under the magnetic attraction between the rod stopper 26 and the rear piston 10 until the rear piston 10 is abutted against the cylinder stopper 29 formed in the sampling cylinder 3. After the rear piston 10 is abutted against the cylinder stopper 29, only the front piston 9 moves independently to its back dead center, as indicated by the two dot-and-dashed line and the solid line in FIG. 2.

In this stroke, the rear piston 10 is released forcedly from magnetic attraction to the red stopper 26, and attracted via the piston main body 20 to the cylinder stopper 29 under the action of the magnet 22 in the abutted state. In other words, the magnet 22 of the rear piston 10 functions as a first magnet for magnetically attracting the rear piston 10 to the rod stopper 26 and also as a second magnet for magnetically attracting the rear piston 10 to the cylinder stopper 29.

A sampling space 30 surrounded by the sampling cylinder 3 is defined between the pistons 9,10, as shown in FIG. 1. The slurry flowing through the process piping 2 is collected by a predetermined amount into this sampling space 30 under the action of the sampling mechanism 4. The sample slurry is compressed when the front piston 9 moves from the position indicated by the two dot-and-dashed line to the position indicated by the solid line shown in FIG. 2 to reduce the volume of the sampling space 30 to about ½ so as to allow only the filtrate in the sample slurry to be fed into the filtrate collecting tank 6, where pH, conductivity, etc. of the filtrate are measured by the sensor 8.

After completion of measurement with the sensor 8, the filtrate is assumed to be returned in the total amount to the sampling space 30 by moving the front piston 9 from the position indicated by the solid line to the position indicated by the two dot-and-dashed line in FIG. 2, to allow the sampling space 30 to resume the original volume while the filter 5 being back-washed by the filtrate. The sample slurry which is recombined with the filtrate is returned to the process piping 2 by the sampling mechanism 4. This latter process will be detailed later.

The filtrate collecting tank 6 is connected via the filter 5 perpendicularly to the upper side of the sampling cylinder 3 extended in the horizontal direction, as shown in FIG. 1, and the sensor 8 is detachably inserted from the upper opening of the tank 6.

As shown in FIG. 1, a cleaning device 31 is disposed on the lower circumference of the filtrate collecting tank 6, for cleaning the sensor 8 succeeding to each filtrate measurement. Even if the sensor 8 is contaminated by the previous run of filtrate measurement, the sensor 8 is cleaned by this cleaning device 31 to prevent the next run from being affected by the contaminants, and thus measurement accuracy can be improved.

Figure 3:
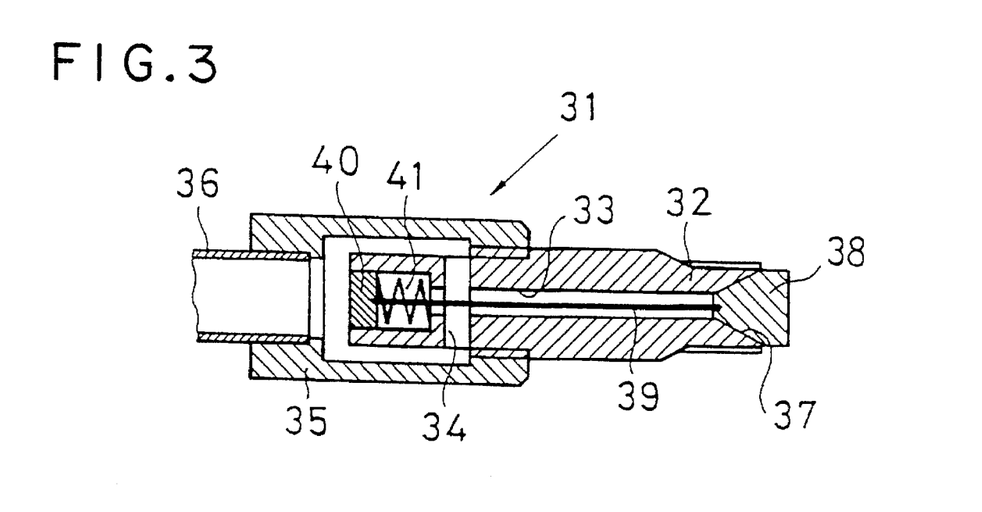
FIG. 3 is a cross-sectional view showing a detailed portion of the cleaning device.

The cleaning device 31 contains a cleaning nozzle 32 having an axial hole 33 and a radial hole 34, which communicates to the inside of the filtrate-collecting tank 6, as shown in FIGS. 1 and 3. A connector 35 is attached to the rear end portion of the cleaning nozzle 32 in such a way that the radial hole 34 may be enveloped by it. Wash water from a wash water-supply pipe 36 is fed through the connector 35 to the cleaning nozzle 32 and is discharged from the tip of the axial hole 33.

A reverse tapered opening 37 where the inner diameter increases gradually outward is provided at the tip of the axial hole 33 of the cleaning nozzle 32, as shown in FIG. 3, and a plug 38 is applied to this reverse tapered opening 37.

As shown in FIG. 3, the distal end of a connecting string 39 disposed in the axial hole 33 is connected to the plug 38, and the proximal end of the connecting string 39 is connected to a stopper block 40 which is normally pressed in the direction of closing the reverse tapered opening 37 with the plug 38 under the urging force of a spring 41. Accordingly, the plug 38 is adapted to open the reverse tapered opening 37 by the discharge pressure of the wash water when it is supplied. Even if the cleaning nozzle 32 is situated at such a position as it is submerged in the filtrate, the tip of the cleaning nozzle 32 can be opened and closed with the plug 38 to avoid such inconveniences that the axial hole 33 is too clogged to be cleaned.

The washing discharge pipe 7, which discharges the wash water used for cleaning the sensor 8 outside through the filter 5 and the sampling cylinder 3, is provided on the lower side of the sampling cylinder 3, as shown in FIG. 1. This pipe 7 contains a normally-open closing valve 42 which is operated by a manipulation handle 43. This closing valve 42 is closed when water supplied from a feed water nozzle 44 is to be fed through the sampling cylinder 3 and the filter 5 into the filtrate collecting tank 6 to allow the sensor 8 to be submerged in the water.

Next, actions of this embodiment will be described referring to FIGS. 4 to 10.

Figure 4:
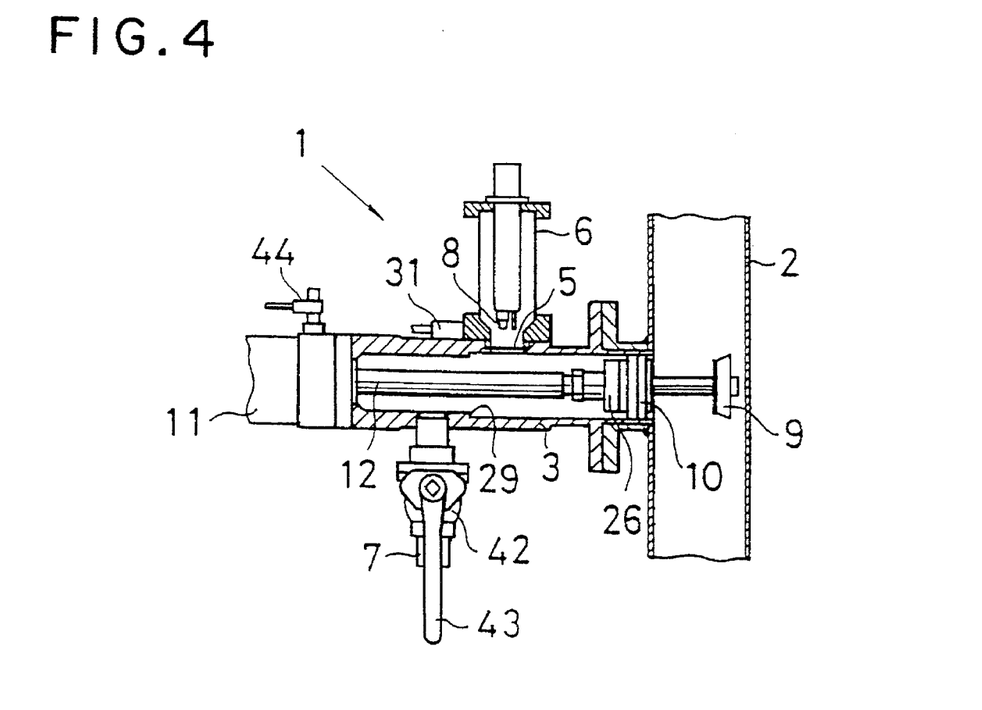
FIG. 4 is a view explaining an operation of the apparatus assuming the initial state.

FIG. 4 shows an initial state of the filtrate measuring apparatus 1, where the front piston 9 is located in the process piping 2, and the rear piston 10 is located at the distal end portion of the sampling cylinder 3 to close the sampling cylinder 3.

Figure 5:
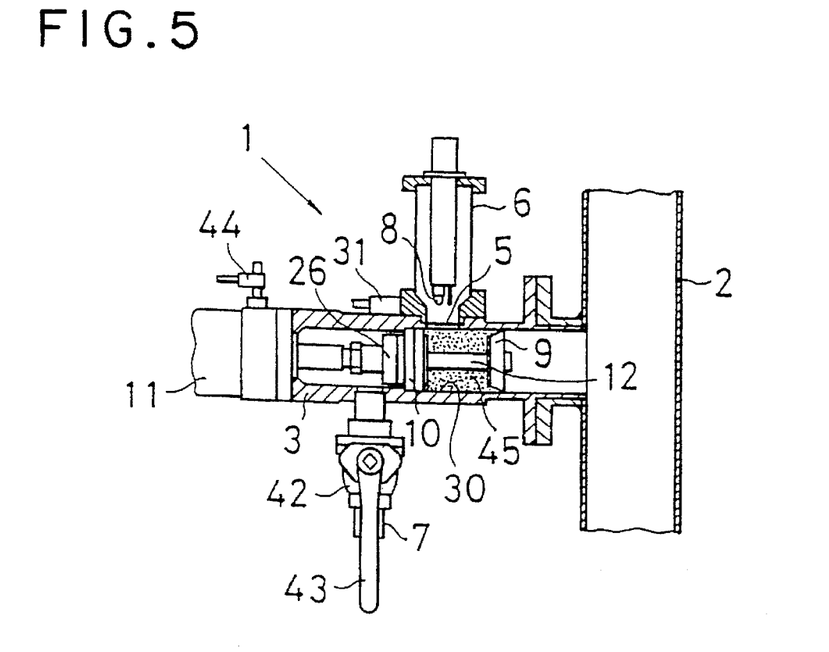
FIG. 5 is a view explaining an operation of the apparatus in which the slurry is collected.

In this state, when the slurry flowing through the process piping 2 is to be collected in a predetermined amount into the sampling cylinder 3, the fluid pressure cylinder 11 is operated to retract the driving rod 12 toward the fluid pressure cylinder 11. In this process, since the rear piston 10 is magnetically attracted to the rod stopper 26 and immobilized on the driving rod 12, the pistons 9,10 retract simultaneously until the rear piston 10 is abutted against the cylinder stopper 29. Accordingly, a predetermined volume can be secured in the sampling space 30 defined by the pistons 9,10 and the sampling cylinder 3, and a predetermined amount of slurry can be collected as a sample slurry 45 into the predetermined volume of sampling space 30, as shown in FIG. 5.

Figure 6:
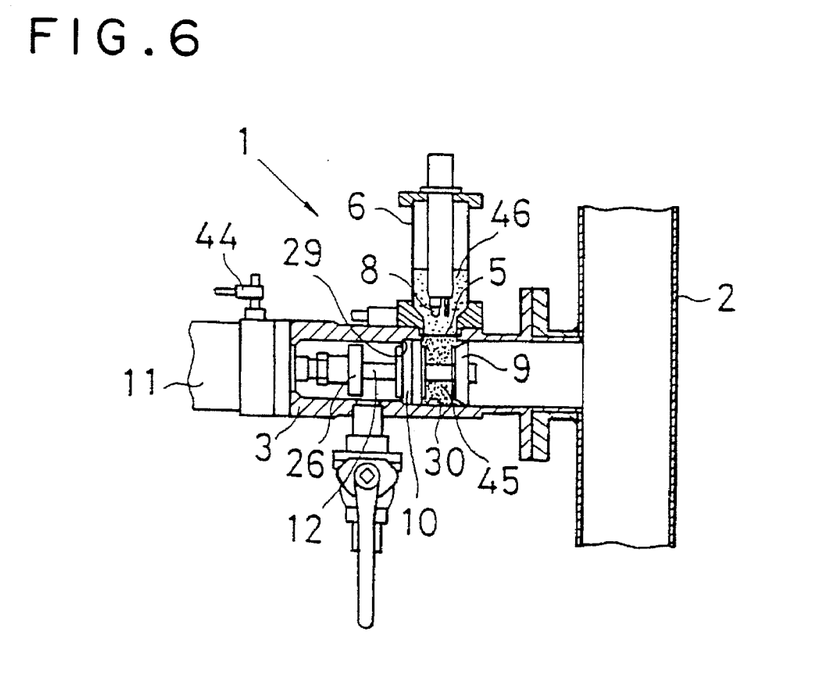
FIG. 6 is a view explaining an operation of the apparatus in which the volume of the sampling space is reduced.

When the driving rod 12 is retracted further with the rear piston 10 being abutted against the cylinder stopper 29, the rear piston 10 cannot retract any further, so that magnetic attraction between the rear piston 10 and the rod stopper 26 is released forcedly, and only the front piston 9 retracts, as shown in FIG. 6. Thus, the volume of the sampling space 30 is reduced, and the sample slurry 45 is pressurized to allow only the filtrate 46 in the sample slurry 45 to be fed through the filter 5 into the filtrate collecting tank 6, where pH, conductivity, etc. of the filtrate 46 are measured by the sensor 8.

Figure 7:
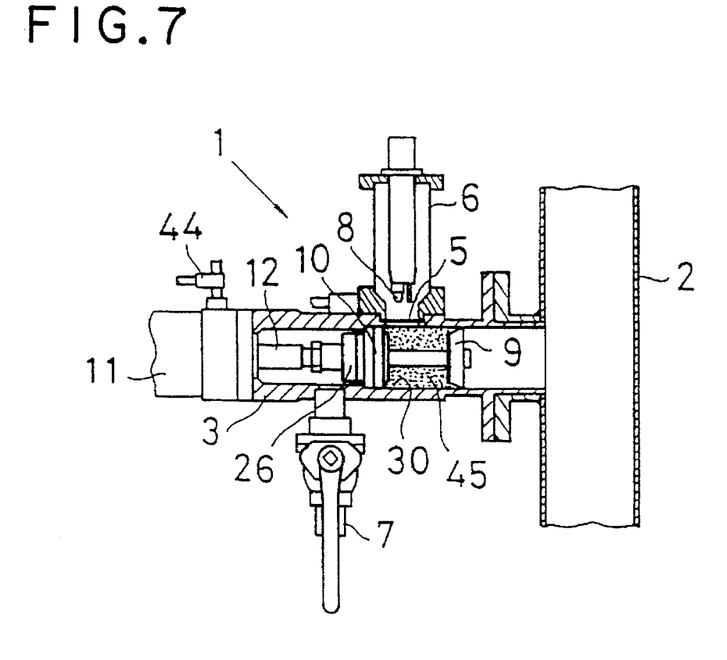
FIG. 7 is a view explaining an operation of the apparatus in which the volume of the sampling space is expanded.

After completion of measurement of the filtrate 46 by the sensor 8, the driving rod 12 is advanced toward the process piping 2, and thus the front piston 9 is advanced together with the driving rod 12. Being magnetically attracted to the cylinder stopper 29, the rear piston 10 remains as such until the rod stopper 26 is abutted against the rear side of the rear piston 10, as shown in FIG. 7. Consequently, only the front piston 9 advances to expand the sampling space 30 and reduce the internal pressure of the sampling space 30. Accordingly, since the filtrate 46 shown in FIG. 6 is returned forcedly in the total amount through the filter 5 into the sampling space 30, the filter 5 can be back-washed by the filtrate 46.

Figure 8:
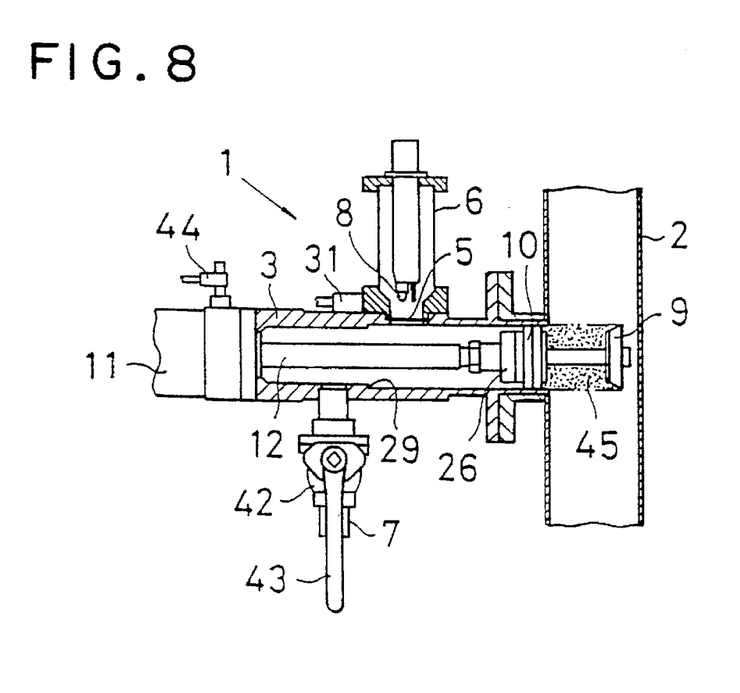
FIG. 8 is a view explaining an operation of the apparatus in which the sample slurry is returned to the process piping.

When the driving rod 12 is advanced further after the filtrate 46 is returned to the sampling space 30, the rear piston 10 magnetically attracted to the rod stopper 26, is pressed on the rear side by the rod stopper 26, so that the magnetic attraction between the rear piston 10 and the cylinder stopper 29 is released forcedly to allow the pistons 9,10 to advance simultaneously together with the driving rod 12. The sample slurry 45 is discharged into the process piping 2 by advancing the front piston 9 to the front dead center, as shown in FIG. 8. The sample slurry 45 is stirred in the sampling space 30 when the filtrate 46 in the filtrate collecting tank 6 is returned to the sampling space 30, so that there occurs no inconvenience that the solid content aggregated into bigger masses is present as such when the slurry 45 is returned into the process piping 2.

Figure 9:
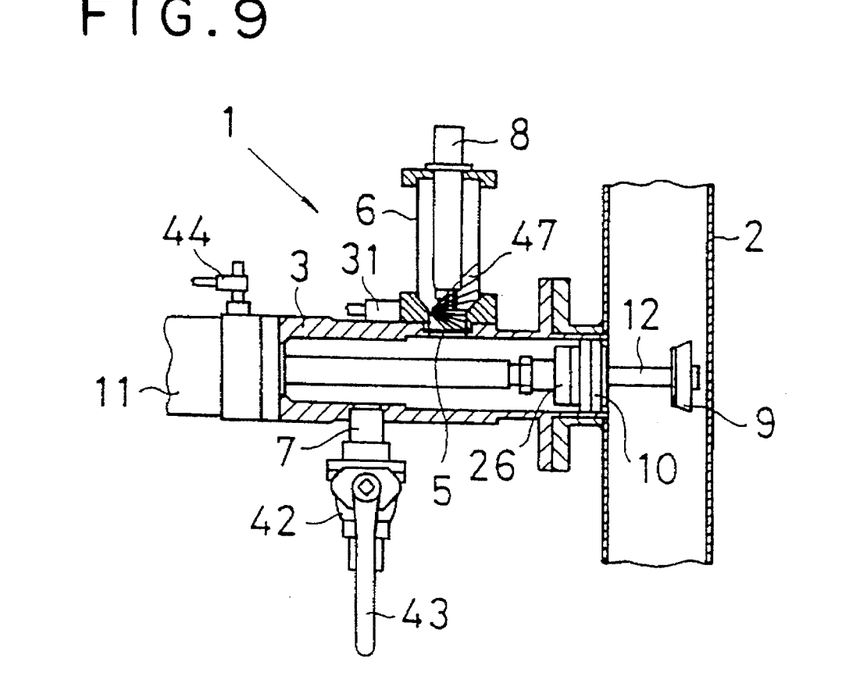
FIG. 9 is a view explaining an operation of the apparatus in which the sensor is being cleaned.

After the sample slurry 45 is returned to the process piping 2, wash water 47 is injected from the cleaning device 31 to clean the sensor 8, as shown in FIG. 9. The wash water 47 resulted after cleaning of the sensor 8 flows through the filter 5 into the sampling cylinder 3, and is discharged through the washing discharge pipe 7 to the outside of the process piping 2. In this process, if the washing discharge pipe 7 is subjected to suction, the washing 47 can be discharged more speedily and completely.

The actions described above are repeated to carry out filtrate measurement at regular intervals or, as necessary, at irregular intervals.

If filtrate measurement is not to be performed for a long time in the apparatus assuming the initial state as shown in FIG. 4, the sensor 8 is liable to be dried. If the sensor 8 is dried, the sensor 8 is likely to be damaged to be unable to give measurement results with high accuracy.

Figure 10:
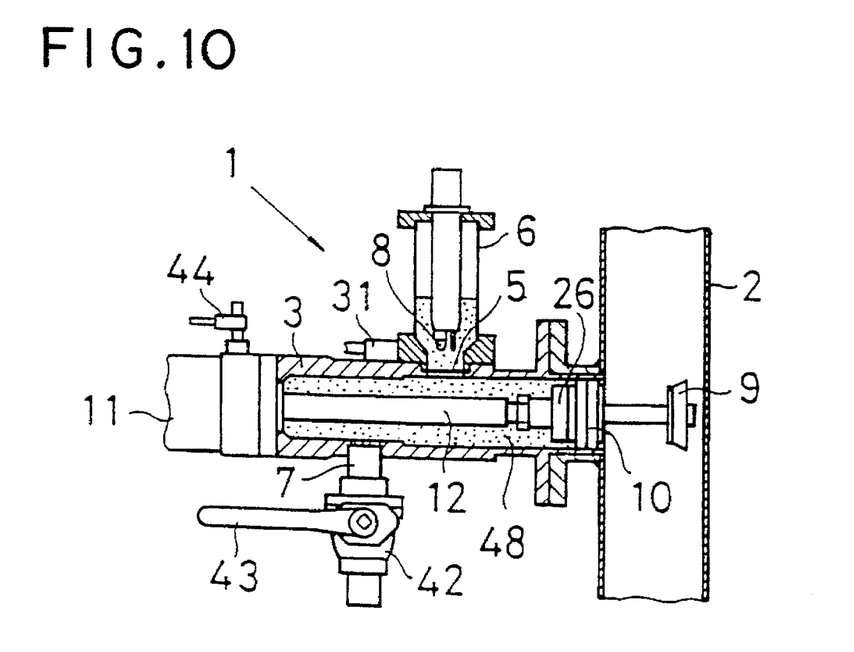
FIG. 10 is a view explaining an operation of the apparatus in which the sensor is submerged in water.

In this embodiment, if filtrate measurement is not to be performed for a long time, the manipulation handle 43 is operated to close the closing valve 42, as shown in FIG. 10, so that water 48 may be supplied from the water supply nozzle 44 into the sampling cylinder 3. Water 48 fills the sampling cylinder 3 and then flows through the filter 5 into the filtrate collecting tank 6 to submerge the sensor 8 In the water.

Incidentally, the filtrate collecting tank 6 has an overflow port (not shown) at a position slightly higher than the liquid surface of a filtrate 46 (see FIG. 6). After increase of the water level to the level of the overflow port, water 48 is discharged from the overflow port. After confirming thet the water 48 is being discharged from the overflow port, supply of the water from the water supply nozzle 44 is stopped.

As described above, the filter 5 is back-washed by the filtrate 46 after each filtrate measurement of the filtrate 46 and also by the washing 47 resulted after cleaning of the sensor 8, so that the filter 5 can be constantly maintained clean. Further, since the filter 5 is kept away from contact with the slurry flowing through the process piping 2, the solid content in the slurry does not inconveniently deposit on the filter 5 to clog it irrespective of its kind.

While the sensor 8 is cleaned by the cleaning device 31 after each filtrate measurement in the embodiment the cleaning device 31 may be omitted in the cases where high accuracy measurement results can be expected even if the sensor 8 is not cleaned.

While the pistons 9,10 are driven by the single fluid pressure cylinder 11 in the embodiment, these pistons 9,10 may be driven by individual fluid pressure cylinders respectively or may be driven by a driving source other than the fluid pressure cylinder.

While the volume of the sampling space 30 is expanded or reduced by changing the span between these two pistons 9,10 in the embodiment, the volume of the sampling space 30 may be reduced and expanded, for example, by inserting and withdrawing an extra member which is different from the pistons 9,10 to and from the sampling space 30.

While filtrate measurement with respect to raw pulp is mainly described in the foregoing embodiment, the present invention can be applied likewise to any slurries other than of raw pulp, for example, of organic sludge and so on, and similar effects can be expected.

Figure 11:
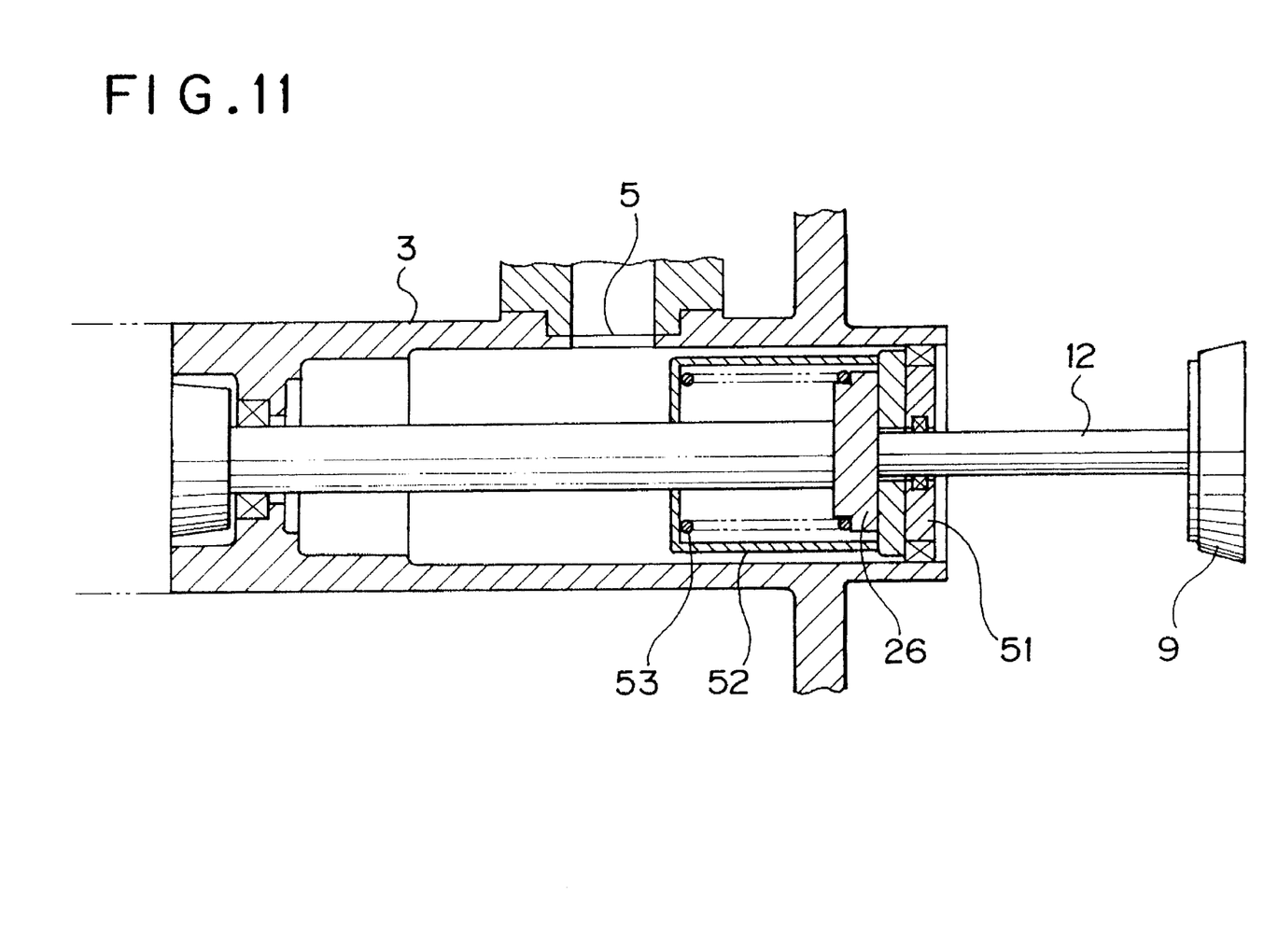
FIG. 11 is a cross-sectional view showing a detailed portion of the filtrate measuring apparatus according to another embodiment.
Figure 12:
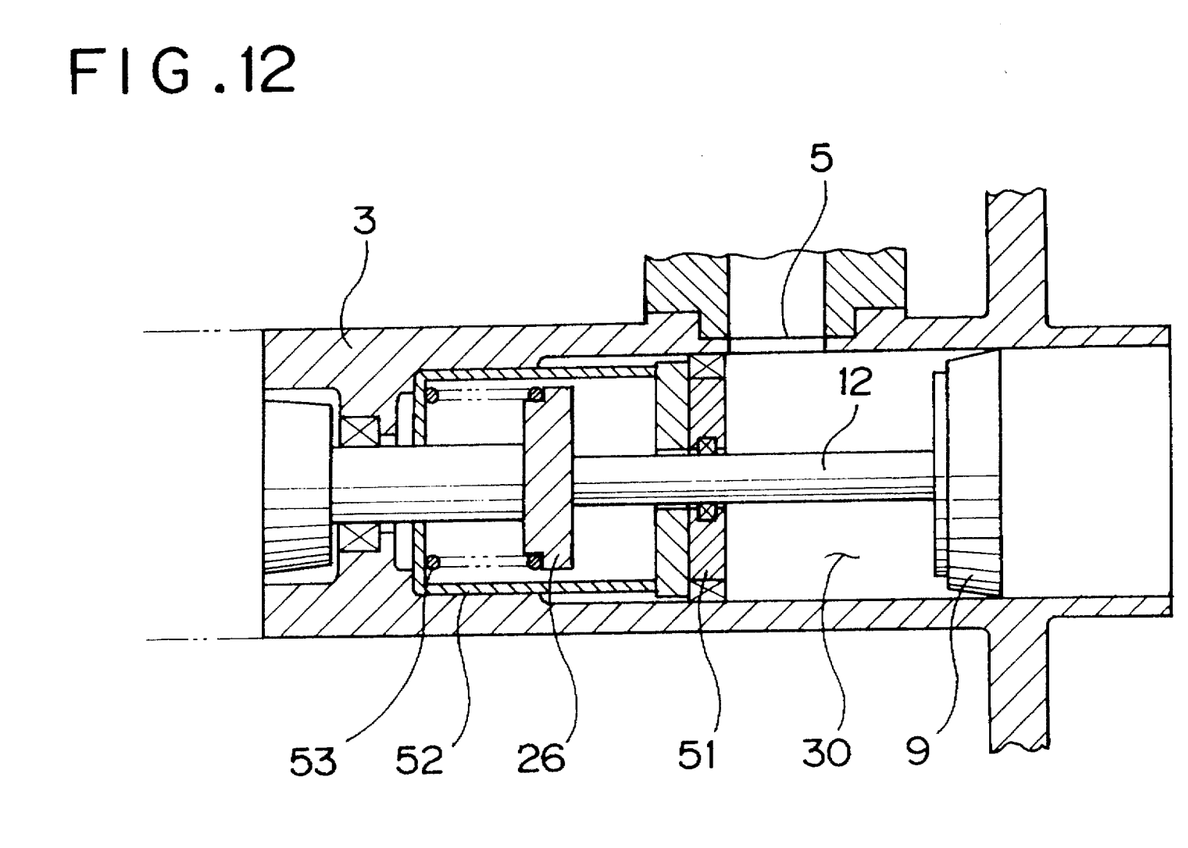
FIG. 12 is a view showing a state both front and back pistons retracted from the state illustrated in FIG. 11.

Another embodiment will be described hereinafter. As shown in FIG. 11, a main portion of a filtrate measuring apparatus in this embodiment is provided with a spring holder 52 extending backwardly from the rear side of a rear piston 51, and a spring 53 supported between the spring holder 52 and the rod stopper 26. The spring holder 52 and spring 53 function equally to the magnet 22 and cylinder stopper 29 of the filtrate measuring apparatus 1 in the first embodiment. Concretely, when the rear piston 51 is retracted to form the sampling space 30 between the rear piston 51 and the front piston 9 in order to collect a specific amount of slurry in the sampling cylinder 3 while maintaining specific space, retraction power of the driving rod 12 is transmitted to the rear piston 51 via elasticity of the spring 53, and as shown in FIG. 12, when the rear piston 51 is retracted to a predetermined position, the spring holder 52 is abutted against the rear end of the sampling cylinder 3 and the driving rod 12 is continuously retracted while compressing the spring 53 to reduce the volume of the sampling space 30.

As has been described heretofore, a predetermined amount of slurry is collected into the sampling space under the sliding motion of the sampling mechanism, and then the volume of the sampling space is reduced to feed only the filtrate to the filtrate collecting tank where the filtrate is measured, followed by expansion of the volume of the sampling space to return the filtrate in the filtrate collecting tank into the sampling space while the filter is back-washed with the filtrate. Accordingly, there is no fear that properties of the slurry in the process piping are changed, and the filter can be maintained clean constantly by the back-washing unlike the case where only the filtrate is collected into the apparatus. Further, since the filter is kept away from contact with the slurry flowing through the process piping, the solid content in the slurry does not inconveniently deposit on the filter to clog it, irrespective of the kind of slurry.

The sample slurry in the sampling space which is recombined with the filtrate in the filtrate collecting tank is adapted to be returned to the process piping according to the present invention, post-treatment is easier compared with the case where the sample slurry is discharged to other places and treated there. Besides, the amount of the slurry to be fed through the process piping to the subsequent step does not inconveniently decrease, even if filtrate measurement is performed frequently.

According to the present invention, since the sensor is cleaned after each filtrate measurement, accuracy of filtrate measurement can be improved. Besides, since the resulting wash water is adapted to be discharged outside the process piping, properties of the slurry in the process piping are not changed by the wash water.

According to the present invention, the sampling mechanism which slides within the sampling cylinder not only collects the slurry and returns it to the process piping but also feeds the filtrate in the collected slurry into the filtrate collecting tank and returns the filtrate in the filtrate collecting tank into the sampling space by reducing and expanding the volume of the sampling space. Accordingly, measurement of all sorts of filtrates can be carried out accurately using the simple structure, and the filter can be constantly maintained clean by the back-washing. Besides, post-treatment of the sample slurry is easy.

According to the present invention, a front piston and a rear piston are incorporated into the sampling mechanism to define the sampling space between these pistons together with the sampling cylinder, collection of the slurry into the sampling space and returning of the sample slurry to the process piping can be carried out by merely reciprocating these two pistons. Further, since the volume of the sampling space can be expanded and reduced by changing the span between these pistons, the structure of the sampling mechanism can be simplified.

According to the present invention, since the front piston is directly driven by the driving rod, and the rear piston is driven indirectly by the driving rod via the first and second magnets, these two pistons can be driven by the single driving rod, although these pistons act in different manners.

According to the present invention, the filtrate collecting tank is provided with a cleaning means for cleaning the sensor after each filtrate measurement. Thus, even if the sensor is contaminated in the previous run of filtrate measurement, the next run is not adversely affected, end thus measurement accuracy can be improved.

According to the present invention, the tip of the cleaning nozzle is adapted to be opened and closed by a plug, so that there is no inconvenience that the cleaning nozzle is clogged to be prevented from duly performing cleaning, even if the cleaning nozzle is situated at such a position as it is submerged in the filtrate.

According to the present invention, the filtrate collecting tank is connected via the filter onto the upper side of the sampling cylinder disposed horizontally, and a discharge section is provided on the lower side of the sampling cylinder. Thus, not only the filter can be cleaned with the wash water resulted after cleaning of the sensor, but also post-treatment of the wash water is easy.

What is claimed is:

1. A filtrate measuring process which comprising:
    employing a sampling cylinder connected to a process piping for feeding a slurry, a filtrate collecting tank connected via a filter to said sampling cylinder, a filtrate measuring sensor attached to the inside of said filtrate collecting tank, and a sampling mechanism having a sampling space and sliding within said sampling cylinder;
    collecting a predetermined amount of slurry from said process piping;
    reducing the volume of said sampling space to feed only the filtrate in the sample slurry to said filtrate collecting tank where measurement of said filtrate is performed; and
    expanding the volume of said sampling space to return said filtrate in said filtrate collecting tank to said sampling space under back-washing of said filter with said filtrate.

2. The filtrate measuring process according to claim 1, wherein said sample slurry in said sampling space which is recombined with the filtrate in said filtrate collecting tank is returned to said process piping.

3. The filtrate measuring process according to claim 2, wherein said sensor is cleaned with wash water after the filtrate measurement, and the resulting wash water is discharged outside said process piping.

4. The filtrate measuring process according to claim 1, wherein said sensor is cleaned with wash water after the filtrate measurement, and the resulting wash water is discharged outside said process piping.

5. A filtrate measuring apparatus comprising:
    a sampling cylinder connectable to a process piping for feeding a slurry;
    a filtrate collecting tank connected via a filter to said sampling cylinder;
    a filtrate measuring sensor attached to the inside of said filtrate collecting tank; and
    a sampling mechanism containing a sampling space and sliding within said sampling cylinder to collect a slurry from said process piping into said sampling space and to return the collected sample slurry to said process piping, as well as, to feed the filtrate in said sample slurry to said filtrate collecting tank and to return said filtrate in said filtrate collecting tank into said sampling space by expanding or reducing the volume of said sampling space.

6. The filtrate measuring apparatus according to claim 5, wherein said sampling mechanism has a front piston reciprocating between said sampling cylinder and said process piping and a rear piston reciprocating within said sampling cylinder; said two pistons and said sampling cylinder defining said sampling space.

7. The filtrate measuring apparatus according to claim 6, wherein said sampling mechanism contains a driving rod slidably penetrating said rear piston and connected at the front end to said front piston to reciprocate said front piston; a rod stopper provided on said driving rod, abutted against the rear side of said rear piston when said driving rod is advanced toward said process piping; a first magnet provided at least on one of said rod stopper and said rear piston, for magnetically attracting said rear piston to said rod stopper; a cylinder stopper provided on said sampling cylinder, to which the rear side of said rear piston is abutted when said driving rod is retracted; and a second magnet provided at least on one of said cylinder stopper and the rear piston, for magnetically attracting said rear piston to said cylinder stopper.

8. The filtrate measuring apparatus according to claim 7, wherein said filtrate collecting tank has a cleaning means for cleaning said sensor after filtrate measurement.

9. The filtrate measuring apparatus according to claim 8, wherein said cleaning means contains a cleaning nozzle for injecting wash water; a plug for opening and closing the tip of said cleaning nozzle; and a spring for normally urging said plug in the closing direction; said plug being let open against the urging force of said spring by the discharge pressure of the wash water.

10. The filtrate measuring apparatus according to claim 9, wherein said sampling cylinder is disposed horizontally, and said filtrate collecting tank is connected via a filter to the upper side of said sampling cylinder; with a discharge section being provided on the lower side of said sampling cylinder, through which the wash water resulted after cleaning of said sensor is discharged via said filter and said sampling cylinder.

11. The filtrate measuring apparatus according to claim 8, wherein said sampling cylinder is disposed horizontally, and said filtrate collecting tank is connected via a filter to the upper side of said sampling cylinder; with a discharge section being provided on the lower side of said sampling cylinder.

12. The filtrate measuring apparatus according to claim 6, wherein the sampling mechanism contains a driving rod slidably penetrating the rear piston and connected at the front end to the front piston to reciprocate the front piston; a rod stopper provided on the driving rod and abutted against the rear side of the rear piston when the driving rod is advanced toward the process piping; a spring holder extended backwardly from the rear side of the rear piston by a predetermined length; and a spring retained between the spring holder and the rod stopper.

13. The filtrate measuring apparatus according to claim 12, wherein said filtrate collecting tank has a cleaning means for cleaning said sensor after filtrate measurement.

14. The filtrate measuring apparatus according to claim 13, wherein said cleaning means contains a cleaning nozzle for injecting wash water; a plug for opening and closing the tip of said cleaning nozzle; and a spring for normally urging said plug in the closing direction; said plug being let open against the urging force of said spring by the discharge pressure of the wash water.

15. The filtrate measuring apparatus according to claim 14, wherein said sampling cylinder is disposed horizontally, and said filtrate collecting tank is connected via a filter to the upper side of said sampling cylinder; with a discharge section being provided on the lower side of said sampling cylinder, through which the wash water resulted after cleaning of said sensor is discharged via said filter and said sampling cylinder.

16. The filtrate measuring apparatus according to claim 13, wherein said sampling cylinder is disposed horizontally, and said filtrate collecting tank is connected via a filter to the upper side of said sampling cylinder; with a discharge section being provided on the lower side of said sampling cylinder.

17. The filtrate measuring apparatus according to claim 6, wherein said filtrate collecting tank has a cleaning means for cleaning said sensor after filtrate measurement.

18. The filtrate measuring apparatus according to claim 17, wherein said cleaning means contains a cleaning nozzle for injecting wash water; a plug for opening and closing the tip of said cleaning nozzle; and a spring for normally urging said plug in the closing direction; said plug being let open against the urging force of said spring by the discharge pressure of the wash water.

19. The filtrate measuring apparatus according to claim 18, wherein said sampling cylinder is disposed horizontally, and said filtrate collecting tank is connected via a filter to the upper side of said sampling cylinder; with a discharge section being provided on the lower side of said sampling cylinder, through which the wash water resulted after cleaning of said sensor is discharged via said filter and said sampling cylinder.

20. The filtrate measuring apparatus according to claim 17, wherein said sampling cylinder is disposed horizontally, and said filtrate collecting tank is connected via a filter to the upper side of said sampling cylinder; with a discharge section being provided on the lower side of said sampling cylinder.

21. The filtrate measuring apparatus according to claim 5, wherein said filtrate collecting tank has a cleaning means for cleaning said sensor after filtrate measurement.

22. The filtrate measuring apparatus according to claim 21, wherein said cleaning means contains a cleaning nozzle for injecting wash water; a plug for opening and closing the tip of said cleaning nozzle; and a spring for normally urging said plug in the closing direction; said plug being let open against the urging force of said spring by the discharge pressure of the wash water.

23. The filtrate measuring apparatus according to claim 22, wherein said sampling cylinder is disposed horizontally, and said filtrate collecting tank is connected via a filter to the upper side of said sampling cylinder; with a discharge section being provided on the lower side of said sampling cylinder, through which the wash water resulted after cleaning of said sensor is discharged via said filter and said sampling cylinder.

24. The filtrate measuring apparatus according to claim 21, wherein said sampling cylinder is disposed horizontally, and said filtrate collecting tank is connected via a filter to the upper side of said sampling cylinder; with a discharge section being provided on the lower side of said sampling cylinder.

* * * * *